United States Patent [19]
Bosslet et al.

[11] Patent Number: 5,935,995
[45] Date of Patent: Aug. 10, 1999

[54] PRODRUGS FOR THE THERAPY OF TUMORS AND INFLAMMATORY DISORDERS

[75] Inventors: Klaus Bosslet; Jörg Czech; Manfred Gerken; Rainer Straub, all of Marburg, Germany; Claude Monneret, Paris, France; Jean-Claude Florent, Les Ulis, France; Frederic Schmidt, Vincennes, France

[73] Assignee: Hoechst Aktiengesellschaft, Frankfurt am Main, Germany

[21] Appl. No.: 08/814,655

[22] Filed: Mar. 11, 1997

[30] Foreign Application Priority Data

Mar. 12, 1996 [EP] European Pat. Off. .............. 96103866

[51] Int. Cl.$^6$ .......................... A01N 43/16; C07D 315/00
[52] U.S. Cl. .......................... 514/460; 549/417; 549/420
[58] Field of Search .................................. 549/417, 420; 514/460

[56] References Cited

U.S. PATENT DOCUMENTS

| | | | |
|---|---|---|---|
| 5,284,856 | 2/1994 | Naik et al. | 514/320 |
| 5,532,259 | 7/1996 | Bartlett et al. | 514/378 |
| 5,561,119 | 10/1996 | Jacquesy et al. | 514/34 |

FOREIGN PATENT DOCUMENTS

| | | |
|---|---|---|
| 2081281 | 10/1992 | Canada . |
| 2109259 | 4/1994 | Canada . |
| 0 366 061 B1 | 5/1990 | European Pat. Off. . |
| 0 501 215 A2 | 9/1992 | European Pat. Off. . |
| 0 511 917 A1 | 11/1992 | European Pat. Off. . |
| 0 590 530 A2 | 4/1994 | European Pat. Off. . |
| 595133 | 5/1994 | European Pat. Off. . |
| 0 623 352 A2 | 11/1994 | European Pat. Off. . |
| 0 642 799 A1 | 3/1995 | European Pat. Off. . |
| 0 595 133 A2 | 5/1995 | European Pat. Off. . |
| 0 696 456 A2 | 5/1995 | European Pat. Off. . |
| WO 90/07929 | 7/1990 | WIPO . |
| WO 91/17748 | 11/1991 | WIPO . |
| WO 92/19639 | 11/1992 | WIPO . |

OTHER PUBLICATIONS

Sharma et al., "Antibody Directed Enzyme Prodrug Therapy (ADEPT): A Three Phase System," *Disease Markers*, vol. 9, pp. 225–231, 1991.

Bosslet et al., "A novel one–step tumor–selective prodrug activation system," *Tumor Targeting*, vol. 1, pp. 45–50, 1995.

Blakey et al., "Anti–tumour effects of an antibody—carboxypeptidase G2 conjugate in combination with phenol mustard prodrugs," *British Journal of Cancer*, vol. 72, pp. 1083–1088, 1995.

Bosslet et al., "Tumor–selective Prodrug Activation by Fusion Protein–mediated Catalysis," *Cancer Research*, vol. 54, No. 8, pp. 2151–2159, 1994.

Trinh et al., "Enzyme/Prodrug Gene Therapy: Comparison of Cytosine Deaminase/5–Fluorocytosine Versus Thymidine Kinase/Ganciclovir Enzyme/Prodrug Systems in a Human Colorectal Carcinoma Cell Line," *Cancer Research*, vol. 55. pp. 4408–4812, 1995.

Bagshawe, "Antibody directed anzymes revive anti–cancer prodrugs concept," *Br. J. Cancer*, vol. 56, pp. 531–532, 1987.

Wang et al., "Activation of Glucuronide Prodrugs by Ligand–β–glucuronidase Conjugates for Chemotherapy," *Chem. Abst.* No. 117782q, vol. 121, p. 625, (1994).

*Primary Examiner*—Mukund J. Shah
*Assistant Examiner*—Tamthom N. Truong
*Attorney, Agent, or Firm*—Finnegan, Henderson, Farabow, Garrett & Dunner, L.L.P.

[57] ABSTRACT

Compounds of the formula I $$\text{glycosyl-Y}[-C(=Y)-X-]_p-W(R)_n-Z-C(=Y)\text{-active compound} \qquad (I)$$

are described which are suitable for the treatment of carcinomatous diseases, autoimmune diseases and chronic inflammatory diseases such as rheumatoid arthritis.

16 Claims, No Drawings

PRODRUGS FOR THE THERAPY OF TUMORS AND INFLAMMATORY DISORDERS

DESCRIPTION

The action of pharmaceuticals (drugs) very frequently consists in inhibiting the disease-promoting activity of pathologically overexpressed enzymes, cytokines or other factors in certain disorders. However, the inhibitory action of drugs extends not only to the pharmacological target structures (enzyme, cytokine, factor) in the diseased tissue, but they also inhibit the activities occurring in healthy tissues. The undesirable side effects observed with many drugs result from this. In order to alleviate the side effects of drugs, experimental systems were developed which allow a more selective release of drugs in the diseased tissue. Systems of this type are briefly described below:

The ADEPT system (antibody-directed enzyme prodrug therapy, Bagshawe 1987, Br. J. Cancer. 56: 531–532) is a two-step system in which in a first step an antibody-enzyme conjugate (AEC) is injected i.v. The AEC is retained in the tumor on account of its tumor selectivity, but excreted from the healthy tissues in the course of 2–7 days. The prodrug (a nontoxic drug precursor) injected i.v. in the second step is activated to give the toxic drug in the tumor by the enzymatic activity of the AEC. As a consequence of this tumor-specific prodrug activation, increased drug concentrations are observed in the tumor (5–50-fold) and lower drug concentrations are observed in the healthy tissue in comparison with the standard therapy. This results in a better tolerability and superior therapeutic effects in human tumor xenograft models (Sharma, S. K. et al. 1991, Disease Markers 9: 225–231).

The FMPA concept (fusion protein-mediated prodrug activation) works similarly to the ADEPT system, in which instead of the xenogenic and therefore immunogenic AEC a nonimmunogenic human fusion protein is employed for the tumor-selective prodrug activation (Bosslet et al 1994, Cancer Res. 54: 2151–2159).

In the VDEPT system (vector-dependent enzyme prodrug therapy, Trinh et al. Cancer Res. 55: 4808–4812), a two-step recombinant DNA mixture, prodrugs are also activated in a tumor-selective manner after injection of a vector and expression of a structural gene which codes for an enzyme.

An endogenous activation of prodrugs (glucuronyl-spacer-anthracycline, Jacquessy et al 1991, WO 92/19639) in necrotic tumors and inflammatory processes associated with strong antitumor and antiinflammatory pharmacological effects was described for the first time as PMT (prodrug monotherapy) by Bosslet et al. 1994, Cancer Res. 54: 2151–2159 and 1995, Tumor Targeting 1. 45–50. In the pharmacological processing of the PMT system, it is seen that both the chemistry of the self-eliminating spacer and the hydrophilicity and molar cytotoxicity of the drug components in the prodrug is of crucial importance for the in vivo efficiency.

A further efficiency increase in PMT was observed in combination with substances which induce necroses (EP 0696456 A2). Above all, the use of antibody conjugates with specificity for the VEGF/VEGF receptor complex, covalently bonded to coagulatory proteins, such as, for example, the truncated tissue factor, show particularly good activity in pharmacological in vivo models when combined with suitable prodrugs.

Surprisingly, we have now succeeded in synthesizing prodrugs which, after appropriate endogenous enzymatic activation, are still significantly more active in vivo than the prodrugs described in EP 0511917 A1 and EP 0595133 A2. This superior activity is determined on the one hand by the novel and advantageous chemistry of the spacer, but on the other hand also by the high molar cytotoxicity of the drug components used. The novel advantageous chemistry of the spacer is distinguished in that, in particular with active compounds which are bonded to the spacer via a hydroxyl group, a release of the active compound after enzymatic cleavage of the glycosyl radical takes place by cyclization and elimination of the spacer. By this means, an improved stability of the prodrugs combined, at the same time, with good enzymatic cleavability is achieved. The prodrugs according to the invention are furthermore more stable under physiological conditions than known prodrugs, because they do not release the active compound so rapidly.

The invention relates to prodrugs of the formula I

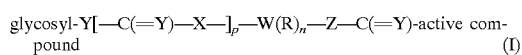

$$\text{glycosyl-Y}[-C(=Y)-X-]_p-W(R)_n-Z-C(=Y)\text{-active compound} \quad (I)$$

and/or physiologically tolerable salts of the compound of the formula I, where glycosyl is an enzymatically cleavable poly-, oligo- or monosaccharide, W is 1) a 5- to 14-membered aromatic radical,
   2) naphthyl,
   3) indenyl,
   4) anthryl,
   5) phenanthryl,
   6) a 5- to 14-membered heterocyclic radical having 1, 2, 3 or 4 heteroatoms from the group consisting of oxygen, nitrogen and sulfur,
   7) ($C_1$–$C_6$)-alkyl,
   8) ($C_2$–$C_6$)-alkenyl,
   9) ($C_3$–$C_6$)-cycloalkyl or
   10) phenyl, R is 1) a hydrogen atom,
   2) ($C_1$–$C_4$)-alkyl,
   3) phenyl,
   4) methoxy,
   5) carboxyl,
   6) methyloxycarbonyl,
   7) —CN,
   8) —OH,
   9) —$NO_2$,
   10) halogen such as fluorine, chlorine or bromine,
   11) sulfonyl,
   12) sulfonamide or
   13) sulfone-($C_1$–$C_4$)-alkylamide, p is zero or 1,
n is zero, 1, 2 or 3,
X is 1) an oxygen atom,
   2) —NH—,
   3) methylenoxy,
   4) methylenamino,
   5) methylene-($C_1$–$C_4$)-alkylamino,
   6) ($C_1$–$C_4$)-alkylamino or
   7) ($C_3$–$C_6$)-cycloalkylamino, Y is an oxygen atom or —NH—,
Z is 1) ($C_1$–$C_4$)-alkylamino,
   2) —N($CH_3$)—,
   3) —C($CH_3$)$_2$—NH—,

4) —CH(CH$_3$)—NH—,

5) —C(CH$_3$)$_2$—N(R$^2$)—, in which R is (C$_1$–C$_4$)-alkyl, or

6) —NH—, if W is (C$_1$–C$_6$)-alkyl, and active compound is a compound having biological action, which is bonded via an oxygen radical, primary or secondary amino radical or an imino radical.

As used herein, the term "enzymatically cleavable" refers to a chemical bond susceptible to enzymatic activation.

If n is the integer 2 or 3, then the radicals R independently of one another have the meanings mentioned in R1) to R13). The term alkyl or alkenyl is understood as meaning radicals whose carbon chain can be straight-chain, branched or cyclic; the double bonds can occur several times. Cyclic alkyl radicals are, for example, 3- to 6-membered monocycles such as cyclopropyl, cyclobutyl, cyclopentyl or cyclohexyl. The term "5- to 14-membered heterocyclic radical having 1, 2, 3 or 4 heteroatoms from the group consisting of oxygen, nitrogen and sulfur" includes, for example, radicals which are derived from pyrrole, azepine, pyrroline, pyridine, imidazole, pyrimidine, triazine, furan, 1,2-diazepine, oxazole, pyrazine, isoxazole, isoxazoline, thiazole, isothiazole, isothiazolidine, indole, quinoline, isoquinoline, benzimidazole, indazole, purine, pteridine, thiopyran or thiophene.

Suitable physiologically tolerable salts of the compounds of the formula I are, for example, alkali metal, alkaline earth metal and ammonium salts, including those of organic ammonium bases. Preferred salts include sodium, potassium, calcium and ammonia salts.

The term monosaccharide is understood as meaning radicals such as D-glucuronyl, L-iduronyl, D-glucopyranosyl-, D-galactopyranosyl, N-acetyl-D-glucosaminyl-, N-acetyl-D-galactosaminyl-, D-mannopyranosyl- or L-fucopyranosyl. Oligo- or polysaccharides consist of 2 to 20 of the abovementioned monosaccharides, which are bonded to one another alpha- or beta-O-glycosidically. The bonding between the monosaccharide and the radical Y is alpha- or beta-glycosidic. Suitable enzymes which effect the cleavage of the glycosyl radical from the radical Y are induronidase, glucosidase, galactosidase, N-acetyl-D-glucosaminidase, N-acetyl-D-galactosaminidase, mannosidase, fucosidase or glucuronidase, preferably β-glucuronidase.

Suitable active compounds are compounds such as anthracycline, preferably doxorubicin, 4'-epidoxorubicin, 4- or 4'-deoxydoxorubicin or a compound preferably selected from the group consisting of etoposide, N-bis(2-chloroethyl)-4-hydroxyaniline, 4-hydroxycyclophosphamide, vindesine, vinblastine, vincristine, terfenadine, terbutaline, fenoterol, salbutamol, muscarine, oxyphenbutazone, salicylic acid, p-aminosalicylic acid, 5-fluorouracil, 5-fluorocytidine, 5-fluorouridine, methotrexate, diclofenac, flufenaminic acid, 4-methylaminophenazone, theophylline, nifedipine, mitomycin C, mitoxantrone, camptothecin, m-AMSA, taxol, nocodazole, colchicine, cyclophosphamide, rachelmycin, cisplatin, melphalan, belomycin, nitrogen mustard gas, phosphoramide mustard gas, quercetin, genistein, erbstatin, tyrphostine, rohitukin derivative ((-)-cis-5,7-dihydroxy-2-(2-chlorophenyl)-8-[4-(3-hydroxy-1-methyl)-piperidinyl]-4H-1-benzopyran-4-one; EP 0 366 061), retinolic acid, butyric acid, phorbol ester, aclacinomycin, progesterone, buserelin, tamoxifen, mifepristone, onapristone, N-(4-aminobutyl)-5-chloro-2-naphthalene-sulfonamide, pyridinyloxazol-2-one, quinolyloxazolone-2-one, isoquinolyloxazolone-2-one, staurosporin, verapamil, forskolin, 1,9-dideoxyforskolin, quinine, quinidine, reserpine, 18-O-(3,5-dimethoxy-4-hydroxybenzoyl) reserpate, lonidamine, buthionine sulfoximine, diethyl dithiocarbamate, cyclosporin A, azathioprine, chlorambucil, N-(4-trifluoromethyl)-phenyl-2-cyano-3-hydroxycrotonamide (WO 91 17748), 15-deoxyspergualin, FK 506, ibuprofen, indomethacin, aspirin, sulfasalazine, penicillinamine, chloroquine, dexamethasone, prednisolone, lidocaine, propafenone, procaine, mefenamic acid, paracetamol, 4-aminophenazone, muskosine, orciprenaline, isoprenaline, amiloride, p-nitrophenylguanidine benzoate or derivatives thereof additionally substituted by one or more hydroxyl, amino or imino groups.

Prodrugs are preferred in which the active compound is a cytostatic, is an antimetabolite, in that the active compound is 5-fluorouracil, 5-fluorocytidine, 5-fluorouridine, cytosine arabinoside or methotrexate, in that the active compound is a substance intercalating in the DNA, in that the active compound is doxorubicin, daunomycin, idarubicin, epirubicin or mitoxantrone, in that the active compound inhibits the topoisomerases I and II, in that the active compound is camptothecin, etoposide or m-AMSA, in that the active compound is a tubulin inhibitor, in that the active compound is vincristine, vinblastine, vindesine, taxol, nocodazole or colchicine, in that the active compound is an alkylating agent, in that the active compound is cyclophosphamide, mitomycin C, rachelmycin, cisplatin, phosphoramide mustard gas, melphalan, bleomycin, nitrogen mustard gas or N-bis(2-chloroethyl)-4-hydroxyaniline, in that the active compound is neocarcinostatin, calicheamicin, dynemicin or esperamicin A, in that the active compound is a compound inactivating the ribosomes, in that the active compound is verrucarin A, in that the active compound is a tyrosine phosphokinase inhibitor, in that the active compound is quercetin, genistein, erbstatin, tyrphostine or a rohitukin derivative, in that the active compound is a differentiation inducer, in that the active compound is retinolic acid, butyric acid, phorbol ester or aclacinomycin, in that the active compound is a hormone, hormone agonist or hormone antagonist, in that the active compound is progesterone, buserelin, tamoxifen, mifepristone or onapristone, in that the active compound is a substance which alters the pleiotropic resistance to cytostatics, in that the active compound is a calmodulin inhibitor, in that the active compound is a protein kinase C inhibitor, in that the active compound is a P-glycoprotein inhibitor, in that the active compound is a modulator of mitochondrially bound hexokinase, in that the active compound is an inhibitor of g-glutamylcysteine synthetase or glutathione-S-transferase, in that the active compound is an inhibitor of superoxide dismutase, in that the active compound is an inhibitor of the proliferation-associated protein defined by the MAb Ki67 in the cell nucleus of a dividing cell, in that the active compound is a substance which exerts immunosuppressant effects, in that the active compound is a standard immunosuppressant, in that the active compound is a macrolide, in that the active compound is cyclosporin A, rapamycin, FK 506, in that the active compound is azothioprine, methotrexate, cyclophosphamide or chlorambucil, in that the active compound is a substance which has antiinflammatory action, in that the active compound is a nonsteroidal antiinflammatory substance, in that the active compound is a "slow acting antirheumatic drug", in that the active compound is a steroid, in that the active compound is a substance which has antiinflammatory, analgesic or antipyretic action, in that the active compound is a derivative of an organic acid, in that the active compound is a nonacidic analgesic/antiinflammatory, in that the active compound is oxyphenbutazone, in that the active compound is a local anesthetic, in that the active compound is an antiarrhythmic, in that the active compound is a Ca++antagonist, in that the active compound is an antihistaminic, in that the active compound is a sympathomimetic or in that the active compound is a substance having inhibitory action on human urokinase; and derivatives of the abovementioned active compounds, where the active compound is bonded to the radical Y of the compound of the formula I via an oxygen radical, —NH radical or imino radical.

The active compound is also preferably the nitrogen mustard gas compound, quinine or dipyridamole mentioned in the Examples.

Prodrugs are preferred where
glycosyl is an enzymatically cleavable glucuronic acid,
W is phenyl,
R is a hydrogen atom, CN, nitro, fluorine, chlorine, bromine,
p is zero,
n is an integer zero, 1 or 2,
Y is an oxygen atom,
Z is —N(CH$_3$)—, —C(CH$_3$)$_2$—NH—, —CH(CH$_3$)—NH—, —C(CH$_3$)$_2$—N(C$_1$–C$_4$)alkyl)—, —CH(CH$_3$)—N(C$_1$–C$_4$)alkyl)— and
active compound is a compound with biological action linked via a hydroxyl, amino or imino group.

Particularly preferred compounds are
2-[N-methyl-N-[(4-(N,N'-bis(2-chloroethyl)amino) phenyloxycarbonyl]-amino]-4-nitrophenyl-β-D-glucuronic acid, 2-[N-methyl-N-[(4-(N,N'-bis(2-iodoethyl)amino) phenyloxycarbonyl]amino]-4-nitrophenyl-β-D-glucuronic acid,

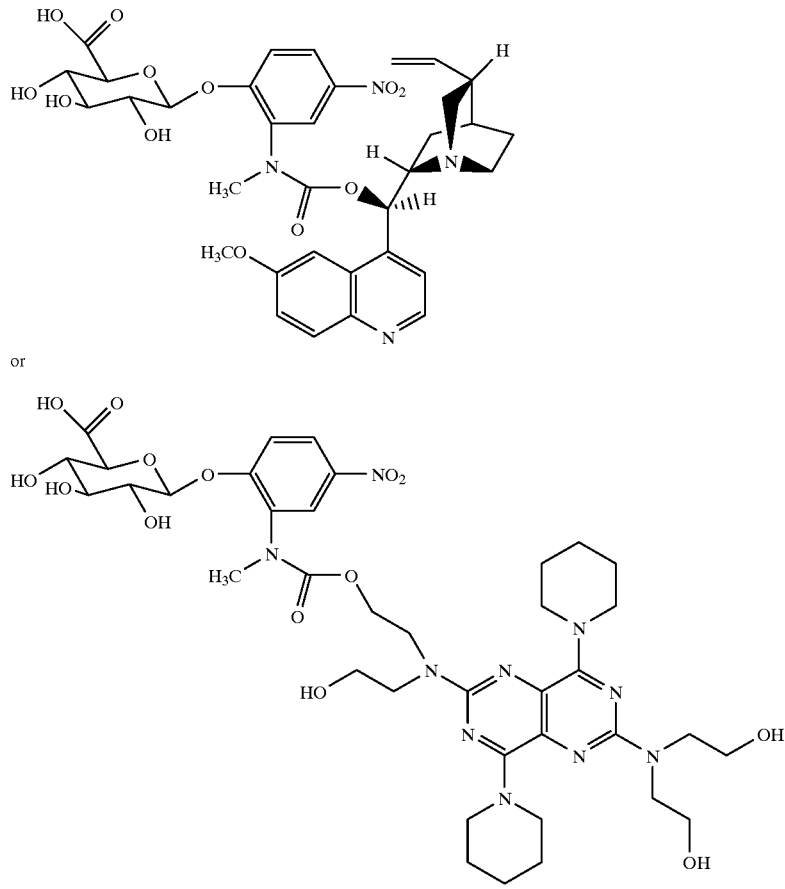

or

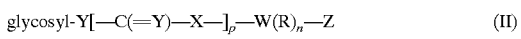

The invention also relates to a process for the preparation of the prodrug of the formula I, which comprises reacting a compound of the formula II $$\text{glycosyl-Y}[-\text{C}(=\text{Y})-\text{X}-]_p-\text{W}(\text{R})_n-\text{Z} \quad \text{(II)}$$

in which the radicals glycosyl, Y, X, p, W, R, n and Z have the meaning mentioned in formula I, with active compound which has an activated carboxyl, amino or imino radical, where the reaction is carried out in the presence of a solvent from the group consisting of acetonitrile, dioxane, tetrahydrofuran, dichloro-methane, dimethylformamide, acetone and the protective groups are then removed hydrolytically.

The activation of the active compound is carried out, for example, according to H. J. Marley, Chem. Soc. Chem. Communication (1987) pages 112–113 or according to H. Hagemann Angew. Chem., 93 (1981) pages 813–814. The removal of the protective groups is carried out, for example, using alkali metal hydroxide solution, alkali metal carbonate, alkali metal cyanide, barium oxide, piperidine or morpholine in the presence of methanol, ethanol or water.

The invention also relates to pharmaceuticals comprising an efficacious amount of at least one compound of the formula I and/or a physiologically tolerable salt of the compound of the formula I, where the radicals glycosyl, Y, X, p, W, R, n, Z and active compound are as defined above, together with a pharmaceutically suitable and physiologically tolerable excipient, additive and/or other active compounds and auxiliaries.

On account of the pharmacological properties, the compounds according to the invention are outstandingly suitable for the prophylaxis and therapy of all those diseases or disorders in whose course intracellular enzymes which can cleave the glycosyl radical are overexpressed and/or released or become available due to cell destruction. These are especially diseases such as cancer, autoimmune diseases or inflammatory, immunologically or metabolically related acute and chronic arthritis and arthropathies, in particular carcinomatous diseases and rheumatoid arthritis.

The invention further relates to the use of the compounds of the formula I for the production of medicaments for the prophylaxis and therapy of carcinomatous diseases, autoimmune diseases and chronic inflammatory diseases such as rheumatoid arthritis.

The invention also relates to a process for the production of a medicament, which comprises bringing at least one compound of the formula I into a suitable administration form with a pharmaceutically suitable and physiologically tolerable excipient and, if appropriate, further suitable active compounds, additives or auxiliaries.

Suitable preparation forms are, for example, injectable solutions, in whose preparation customary auxiliaries, such as excipients, binders, swelling agents or lubricants and solubilizers, are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower, ground nut or sesame oil, polyethylene glycol and solvents such as, for example, sterile water and mono- or polyhydric alcohols such as glycerol. Liposomes or human proteins can also be used as excipients.

The pharmaceutical preparations are preferably prepared and administered in dose units, each unit containing as active constituent a certain dose of the compound of the formula I according to the invention. With injection solutions, this dose for an adult patient of weight approximately 70 kg can be up to approximately 10 g, but preferably approximately from 3 g to 5 g. Under certain circumstances, however, even higher or lower daily doses may be appropriate. The administration of the daily dose can be carried out both by single administration in the form of an individual dose unit or else of several smaller dose units as well as by multiple administration of subdivided doses at certain intervals.

The prodrugs according to the invention can also be employed in all nononcological diseases in which macrophages, granulocytes and platelets occur, in particular in the activated state. In the activated state, the abovementioned cells principally secrete intracellular enzymes, which makes possible a site-specific activation of the prodrugs according to the invention.

In the oncological indication, the activation of the prodrugs according to the invention is effected by intracellular enzymes released from dying tumor cells. This phenomenon occurs especially with larger tumors (diameter more than 0.3 cm), but also after damage to the tumor by treatment with immunotoxins, cytostatics, irradiation, fusion proteins or antibody-enzyme conjugates.

Since the glycosyl moiety of the prodrugs according to the invention is chosen such that it can only be removed from enzymes released locally under pathophysiological conditions, the lipophilic drug may likewise only be released in the target tissue and there display its cytotoxic action.

The superior action of a prodrug according to the invention with a cytotoxic drug component can be increased by combining it with prodrugs according to the invention with another cytotoxic drug component. Prodrug combinations are advantageous here in which cytotoxic components with a different mechanism of action are used, corresponding to poly-chemotherapy. The use of active compounds which produce very efficient single-strand and double-strand breaks in the DNA such as calicheamicin appears particularly suitable. Of particular advantage, however, are prodrug combinations according to the invention in which one drug has cytotoxic potential and the other, however, blocks multidrug resistance.

The invention further relates to pharmaceutical compositions comprising a compound of the formula I and antibody-enzyme conjugates.

Antibody-enzyme conjugates are understood as meaning compounds which bind specifically to tumor tissue or inflamed tissue via the antibody section and have an enzyme section which can cleave the glycosyl radical of the compound of the formula I. Examples of such compounds are described in EP 0 501 215, EP 0 390 530 or EP 0 623 352.

EXAMPLE 1

Nitrogen Mustard Gas Derivative Prodrug (F373; compound 11)

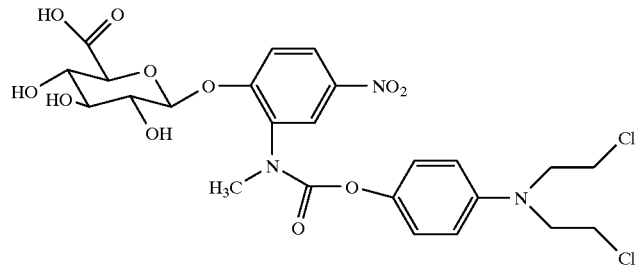

was synthesized in the following way:

The starting material for the synthesis was 2-amino-4-nitrophenol (compound 1). Compound 1 was first monomethylated with the aid of methyl iodide (compound 2) and the amino function was protected as the BOC derivative (compound 3). The protected glucuronic acid was introduced by means of silver oxide coupling of compound 3 and the bromide (compound 4) with obtainment of compound 5. After removal of the BOC protective group with HCl, the amine (compound 6) was obtained. Compound 7 was reacted to give the chloroformate (compound 8) and condensed with compound 6 to give the compound 9. After cleavage of the esters of the glucuronic acid moiety of the compound 3 in two steps (MeONa/MeOH, then aqueous NaOH), the prodrug (compound 11) was obtained via compound 10.
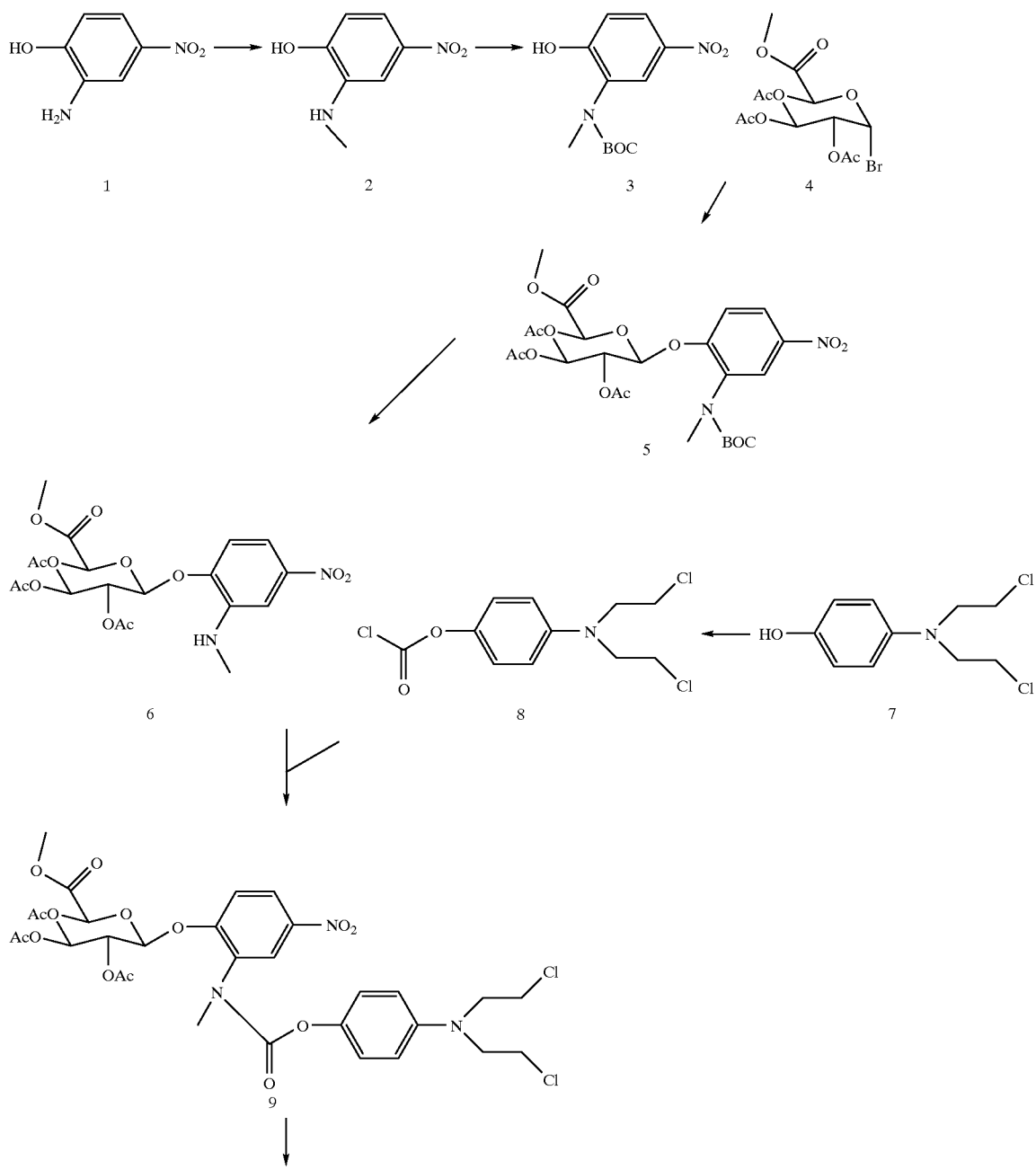

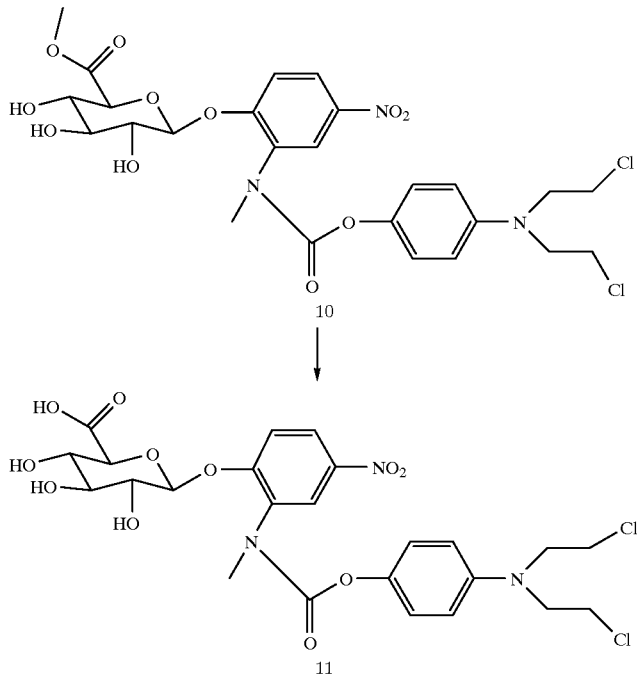

Compound 2
2-(N-Methylamino)-4-nitrophenol (2)

Triethylamine (2 ml, 14.4 mmol) was added to a solution of 2-amino-4-nitrophenol (1) (1.54 g, 10 mmol) and methyl iodide (1 ml, 16 mmol) in methanol (10 ml). After 1 hour at 40° C., further methyl iodide (1 ml) and triethylamine (1 ml) were added and the mixture was stirred at 40° C. for a further 2 hours. The reaction mixture was concentrated to dryness in vacuo, the residue was added to aqueous 2N sodium acetate solution and the mixture was extracted with ethyl acetate. The organic phase was dried with sodium sulfate and chromatographed on silica gel (eluent dichloromethane/methanol 95/5). Yield 880 mg (52%).

$C_7H_8N_2O_3$: Calculated C:50.02 H:4.76 N:16.73 Found C:50.00 H:4.80 N: 16.66

Melting point: 148° C. (toluene).

$^1$H NMR (250 MHz,DMSO): d 7.44)(dd,$J_{ortho}$=9 Hz, $J_{meta}$=3.0 Hz, 1H), 7.13 (d,J=3 Hz, 1H), 6.77 (d,J=9 Hz, 1H), 2.76 (s, 3H).

IR (KBr): n(cm$^{-1}$) 3363(OH), 1538, 1338(NO$_2$).

MS(DCI, NH$_3$):m/z [M+H]$^+$:169.

Compound 3
2-(N-BOC,N-methylamino)-4-nitrophenol (3)

Di-tert-butyl dicarbonate (14 g, 64.15 mmol), potassium carbonate (17 g, 123 mmol) and water (50 ml) were added to a solution of 2-N-methyl-amino-4-nitrophenol (2) (4.18 g, 24.9 mmol) in tetrahydrofuran (50 ml) and the mixture was stirred overnight at room temperature. The reaction mixture was acidified with a saturated aqueous ammonium chloride solution and extracted with ethyl acetate, and the extract was dried with sodium sulfate and concentrated in vacuo. The crude product was stirred with potassium carbonate (17 g, 123 mmol) in methanol (100 ml) for two hours, the mixture was acidified with a saturated aqueous ammonium chloride solution and extracted with ethyl acetate, and the extract was dried with sodium sulfate and concentrated in vacuo. The product was chromatographed on silica gel (eluent dichloromethane/methanol 97.5/2.5). Yield 6.2 g (93%).

$C_{12}H_{16}N_2O_5$: Calculated C:53.72 H:6.01 N:10.44 Found C:53.64 H:6.20 N: 10.36

Melting point: 197° C. (toluene/petroleum ether)

$^1$H NMR (250 MHz,DMSO): d 8.10–8.00 (2H), 7.03 (d, J=8.5 Hz, 1H), 3.04 (s, 3H), 1.40–1.30 (9H).

IR (KBr): n(cm$^{-1}$) 3129 (OH), 1672 (CO), 1529, 1339 (NO$_2$).

MS(DCI, NH$_3$):m/z [M+H]$^+$:269, [M+H-C$_4$H$_8$]$^+$:213, [M+H-C$_4$H$_8$OCO]$^+$:169.

Compound 5
Methyl 2-(N-BOC,N-methylamino)-4-nitrophenyl-2,3,4-tri-O-acetyl-β-D-glucuronate (5)

Silver oxide (0.23 g, 0.992 mmol) and 2-(N-BOC,N-methylamino)-4-nitrophenol (3) were added to a solution of methyl 2,3,4-tri-O-acetyl-a-D-glucuronate bromide (4) (126 mg, 0.317 mmol) in acetonitrile (5 ml). The reaction mixture was stirred at room temperature for 1 hour, filtered through Celite and concentrated in vacuo. The product was chromatographed on silica gel (eluent dichloromethane/methanol 97.5/2.5). Yield 165 mg (89%).

$C_{25}H_{32}N_2O_{14}$: Calculated C:51.37 H:5.52 N:4.79 Found C:51.79 H:5.72 N:4.66

Melting point: 80° C. (toluene/petroleum ether)

$[a]_D^{20}$=−39° (c=1.02 in CHCl$_3$).

$^1$H NMR (250 MHz,CDCl$_3$): d 8.14 (dd, $J_{ortho}$=9 Hz, $J_{meta}$=2.5 Hz,1H), 8.15–8.05 (1H), 7.30–7.20 (1H), 5.45–5.30 (4H), 4.25 (d, J=9Hz, 1H), 3.73 (s, 3H), 3.13 (s, 3H), 2.15–2.05 (9H), 1.65–1.40 (9H).

IR (CDCl$_3$): n(cm$^{-1}$) 1760 (CO, ester), 1699 (CO, carbamate), 1529, 1349(NO$_2$).

MS(DCI, NH$_3$):m/z [M+NH$_4$]$^+$:602.

Compound 6
Methyl 2-(N-methylamino)-4-nitrophenyl-2,3,4-tri-O-acetyl-β-D-glucuronate (6)

A solution of methyl 2-(N-BOC,N-methylamino)-4-nitrophenyl-2,3,4-tri-O-acetyl-β-D-glucuronate (5) (3 g, 5.13 mmol) in 2.12 M hydrochloric acid in ethyl acetate (60 ml) was stirred at room temperature for 1 hour. The solution was added to excess, aqueous, saturated sodium bicarbonate solution and the mixture was extracted with ethyl acetate. The organic phase was dried with sodium sulfate and concentrated. The product was chromatographed on silica gel (eluent dichloromethane/methanol 97.5/2.5). Yield 2.14 g (86%), yellow solid.

$C_{20}H_{24}N_2O_{12}$: Calculated C:49.59 H:4.99 N:5.78 Found C:49.81 H:5.12 N:4.80

Melting point: 120° C. (toluene)

$[a]_D^{20}$=−58° (c=1.04 in $CHCl_3$).

$^1$H NMR (300 MHz,$CDCl_3$): d 7.53 (dd,$J_{ortho}$=8.5 Hz, $J_{meta}$=2.5 Hz,1H), 7.37 (d, J=2.5 Hz, 1H), 6.91 (d, J=8.5 Hz, 1H), 5.45–5.30 (1H), 5.16(d,J=7 Hz, b, 1H), 4.50 (d, J=5 Hz, 1H), 4.24 (d, J=9 Hz, 1H), 3.75 (s, 3H), 2.90 (d, J=5 Hz, 1H), 2.10–2.05 (9H).

IR ($CDCl_3$): n($cm^{-1}$) 3443 (NH), 1758 (CO), 1553, 1346 ($NO_2$).

MS(DCI, $NH_3$):m/z $[M+H]^+$:485.

Compound 8

4-[N,N-bis(2-Chloroethyl)amino]phenyl chloroformate (8)

Phosgene in toluene (1.93 M) (8 ml, 15.4 mmol) was added to a suspension of 4-[N,N-bis(2-chloroethyl)amino] phenol hydrochloride (7) (1.85 mmol) in tetrahydrofuran (30 ml) and the mixture was stirred at 0° C. for 30 minutes. After addition of triethylamine (1 ml, 7.17 mmol), the mixture was stirred at 0° C. for a further hour. The suspension was then filtered and concentrated in vacuo at room temperature. Flash chromatography on silica gel using dichloromethane as an eluent afforded the product as a colorless liquid which was employed immediately in the next reaction. Yield 70%.

$^1$H NMR (250 MHz,$CDCl_3$): d 7.10(d, J=9 Hz, 2H), 6.66 (d, J=9 Hz, 2H), 3.73 (t, J=6.5 Hz, 4H), 3.63 (t, J=6.5 Hz, 4H).

IR ($CDCl_3$): n($cm^{-1}$) 1779 (CO), 1514 (aromatic).

MS(DCI, $NH_3$):m/z [M+H]+:296, $[M+2+H]^+$:298.

Compound 9

Methyl 2-[N-methyl-N-[4-(N,N'-bis(2-chloroethyl)amino) phenyloxy-carbonyl]amino]-4-nitrophenyl-2,3,4-tri-O-acetyl-β-D-glucuronate (9)

Methyl 2-(N-methylamino)-4-nitrophenyl-2,3,4-tri-O-acetyl-β-D-glucuronate (6) (0.50 g, 1.03 mmol) was added to a solution of 4-[N,N-bis(2-chloroethyl)amino]phenyl chloroformate (8) (0.31 g, 1.04 mmol) in tetrahydrofuran (15 ml) and diisopropylethylamine (0.25 ml, 1.44 mmol) and the mixture was refluxed for 2 hours. After cooling to room temperature, it was concentrated. The product was chromatographed on silica gel (eluent dichloromethane/methanol 97.5/2.5). Yield 487 mg (64%).

$C_{31}H_{35}N_3O_{14}Cl_2$: Calculated C:50.00 H:4.74 N:5.64 Cl:9.52 Found C:49.90 H:4.82 N:5.62 Cl:9.78

Melting point: 101° C. (methanol)

$[a]_D^{20}$ =−47° (c=1.10 in $CHCl_3$).

$^1$H NMR (300 MHz,$CDCl_3$): d 8.25–8.15 (2H), 7.45–7.35 (1H), 7.25–7.05 (1H), 6.95–6.85 (1H), 6.70–6.55 (2H), 5.45–5.25 (4H), 4.28 (d, J=9Hz, 1H), 3.80–3.55 (11H), 3.38(s)2 diastereomeric carbamates(40/60) 3H, 3.27 (s), 2.20–2.00 (9H).

IR ($CDCl_3$): n($cm^{-1}$) 1760 (CO, ester), 1722 (CO, carbamate),1530, 1350($NO_2$).

MS(DCI, $NH_3$):m/z $[M+H]^+$:744; $[M+2+H]^+$:746, $[M+Na]^+$:766,$[M+2+Na]^+$:768.

Compound 10

Methyl 2-[N-methyl-N-[4-(N,N'-bis(2-chloroethyl)amino) phenyloxy-carbonyl]amino]-4-nitrophenyl-β-D-glucuronate (10)

Sodium methoxide (2 mg, 0.037 mmol) was added at −15° C. to a suspension of methyl 2-[N-methyl-N-[(4-(N, N'-bis(2-chloroethyl)amino)-phenyloxycarbonyl]amino]-4-nitrophenyl-2,3,4-tri-O-acetyl-β-D-glucuronate (9) (68 mg, 0.0915 mmol) in methanol (5 ml) and the mixture was stirred at −15° C. for 6 hours. After neutralization with ion exchanger (Amberlite IRC-50 S) and filtration, the solution was concentrated and chromatographed on silica gel using ethyl acetate as eluent. Yield 50 mg (89%).

$C_{25}H_{29}N_3O_{11}Cl_2$: [lacuna]

$^1$H NMR (300 MHz,$CDCl_3$): d 8.22 (sl, 1H), 8.16 (d, J=8.5 Hz, 1H), 7.25 (d, 1H), 7.15–6.90 (2H), 6.80–6.45 (2H), 5.06 (1H), 4.09 (1H), 4.20–3.15 (17H).

IR ($CDCl_3$): n($cm^{-1}$) 3601, 3448 (OH),1714 (CO), 1528, 1349 ($NO_2$).

MS(ES):m/z $[M+Na]^+$:640,$[M+2+Na]^+$:642.

Compound 11

2-[N-Methyl-N-[4-(N,N'-bis(2-chloroethyl)amino) phenyloxycarbonyl]-amino]-4-nitrophenyl-β-D-glucuronic acid (11)

0.3 ml of a 1 N aqueous sodium hydroxide solution was added at −15° C. to a solution of compound 10 (50 mg, 0.0809 mmol) in acetone (4 ml). The mixture was stirred at −15° C. for 2 hours, neutralized with 1N aqueous hydrochloric acid and concentrated in vacuo (T<40° C.). The product was chromatographed on silica gel using acetonitrile/water (9/1). The yield was 45 mg (89%).

$C_{24}H_{27}N_3O_{11}Cl_2$ [lacuna]:

$^1$H NMR (250 MHz,$CD_3OD$):

d 8.30 (sl, 1H), 8.24 (dd,$J_{ortho}$=9 Hz, $J_{meta}$2.5 Hz, 1H), 7.52 (d, J=9 Hz, 1H), 6.99 (d, J=9 Hz, 2H), 6.69 (d, J=9 Hz, 2H), 5.23 (1H), 3.89 (d,J=9 Hz, 1H), 3.80–3.33 (1H).

IR (KR): n(cm−1) 3418(OH),1705(CO),1516,1349 ($NO_2$).

MS(ES):m/z $[M-H]^+$:603 $[M+2-H]^+$:605.

EXAMPLE 2

2-[N-Methyl-N-[(4-(N,N'-bis(2-iodoethyl)amino) phenyloxycarbonyl]amino]-4-nitrophenyl-β-D-glucuronic acid (12)

Compound 12

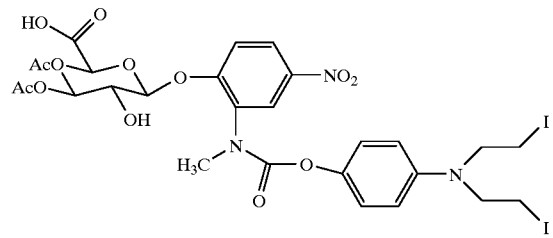

Synthesis was carried out analogously to Example 1.

EXAMPLE 3

Compound 13: Quinine Prodrug (F 391)

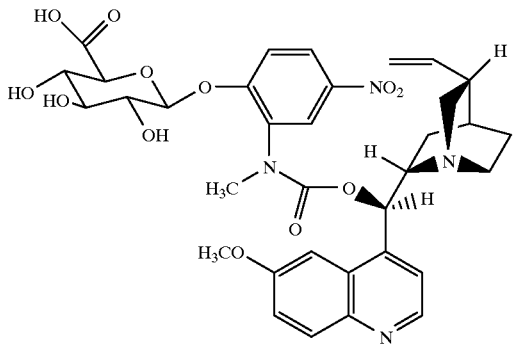

Synthesis was carried out analogously to Example 1.

EXAMPLE 4

Compound 14: Dipyridamole Prodrug (F 392)

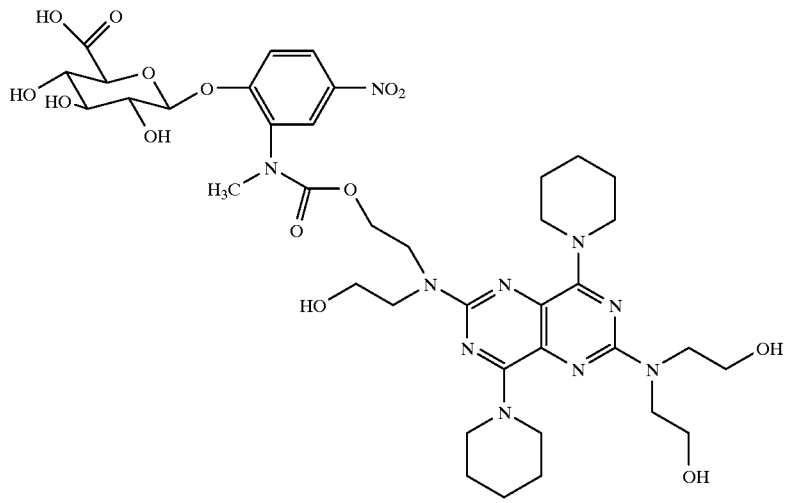

Synthesis was carried out analogously to Example 1.

EXAMPLE 5

Enzymatic Cleavage of F 373

On incubation with b-glucuronidase, the prodrug F 373 (compound 11) is cleaved enzymatically to an aromatic nitrogen mustard gas derivative (4-[N,N-bis(2-chloroethyl) amino]phenol) (compound 7), glucuronic acid and the spacer.

F 373 ® glucuronic acid+

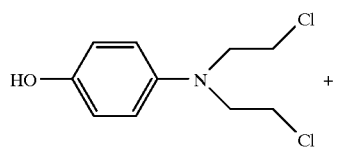

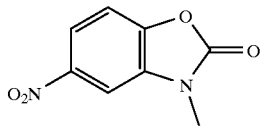

Compound 7 Spacer (compound 15)

The prodrug F 373 is stable in solution in anhydrous DMSO. To investigate the cleavability, 10 ml of F 373 solution (5 mg/ml in DMSO) were treated with 180 ml of 0.02 M phosphate buffer pH 7.2 and 10 ml of *E. coli* β-glucuronidase (Sigma) (330 mg/ml) and the mixture was incubated at 37° C. 25 ml batches were diluted with 225 ml of 0.1 M phosphate buffer pH 3.0 (85%) and acetonitrile (15%) and immediately analyzed with the aid of the following HPLC system.

HPLC System

The HPLC system used consisted of a gradient pump (Gynkotek, Model 480), an autosampler (Abimed, Model 231/401), a UV detector (Beckman, Model 166, detection wavelength 212 nm) and an analysis unit (Beckman, System Gold). The separations were carried out on an RP column (Zorbax SB-C 18, 5 mm, 125×4.6 mm). The mobile phase was formed from two components according to the following scheme:

A—Acetonitrile
B—0.02 M phosphate buffer pH 3.0
0 min: 15% A, 85% B
15 min: 75% A, 25% B
25 min: 75% A, 25% B
27 min: 15% A, 85% B
35 min: 15% A, 85% B.

The following peak areas were found:

| Time min | F 373 RT = 12.6 | compound 7 RT = 10.7 | Spacer compound 15 RT = 14.1 |
|---|---|---|---|
| 0 | 19.41 | 0 | 0 |
| 1 | 10.46 | 3.32 | 1.92 |
| 5 | 0.35 | 7.43 | 4.75 |

-continued

| Time min | F 373 RT = 12.6 | compound 7 RT = 10.7 | Spacer compound 15 RT = 14.1 |
|---|---|---|---|
| 7 | 0 | 7.33 | 5.37 |
| 10 | 0 | 6.79 | 5.43 |
| 15 | 0 | 5.58 | 5.43 |
| 25 | 0 | 4.00 | 5.70 |
| 60 | 0 | 0.88 | 6.53 |

EXAMPLE 6

Cytotoxicity of F 373, 391 and 392 on Tumor Cells in the Presence and Absence of β-glucuronidase $2 \times 10^3$ LoVo cells per well were inoculated into 100 ml of MEM+10% FCS in a 96-well microtiter plate. After 24 h, the test substances were added in 100 ml of medium at the desired concentration and, optionally, additionally β-glucuronidase (50 mg/mil final concentration; Sigma G 7896). Each group consisted of 4 wells; the control was only incubated with medium. After 65 h, 50 ml of MTT (2.5 mg/ml in PBS) were added and the supernatant was removed after 3 h. The dye formed by the living cells was dissolved by addition of 100 ml of DMSO/well. The extinction was measured for each well at 492 nm with the aid of a multiscan photometer 340 CC (Flow). The values of the 4 wells per group were averaged and from this the dose-response curve and the $IC_{50}$ were calculated using GraFit 3.0 software.

| Substance (Prodrug) | without β-gluc. $IC_{50}$ in mmol | with β-gluc. $IC_{50}$ in mmol |
|---|---|---|
| F 373 | >500 | 6.3 |
| F 391 | >400 | 113 |
| F 392 | >400 | 49.5 |

The toxic compound in the prodrug F 373 is the compound 7 (example 1, page 15) and shows an $IC_{50}$ of 5 mmol tested alone. The toxic compound in the prodrug F 391 is quinine and shows an $IC_{50}$ of 103 mmol tested alone. The toxic compound in the prodrug F 392 is dipyridamole and shows an $IC_{50}$ of 43 mmol tested alone.

We claim:

1. A compound of formula I

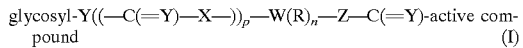

or salt thereof, wherein glycosyl is a poly-, oligo- or monosaccharide;

W is naphthyl, indenyl, anthryl, phenanthryl, $(C_1-C_6)$-alkyl, $(C_2-C_6)$-alkenyl, $(C_3-C_6)$-cycloalkyl, or phenyl;

R is hydrogen, $(C_1-C_4)$-alkyl, phenyl, methoxy, carboxyl, methyloxycarbonyl, —CN, —OH, —$NO_2$, a halogen, sulfonyl, sulfonamide, or sulfone-$(C_1-C_4)$-alkylamide;

p is zero or 1;

n is zero, 1, 2 or 3;

X is oxygen, —NH—, methylenoxy, methylenamino, methylene-$(C_1-C_4)$-alkylamino, $(C_1-C_4)$-alkylamino, or $(C_1-C_4)$-cycloalkylamino;

Y is oxygen or —NH—;

Z is $(C_1-C_4)$-alkylamino, —$N(CH_3)$—, —$C(CH_3)_2$—NH—, —$CH(CH_3)$—NH—, —$C(CH_3)_2$—$N(R^2)$—, in which $R^2$ is $(C_1-C_4)$-alkyl, or —NH—, if W is $(C_1-C_6)$-alkyl; and active compound is a cytostatic, an antimetabolite, a DNA intercalator, a topoisomerase I or II inhibitor, a tubulin inhibitor, an alkylating agent, a ribosome inactivator, a cell differentiation inducer, a hormone, a hormone agonist or antagonist, a calmodulin inhibitor, a P-glycoprotein inhibitor, a modulator of mitochondrially bound hexokinase, a g-glutamylcysteine inhibitor, a glutathione-S-transferase inhibitor, a superoxide dismutase inhibitor, a proliferation-associated protein inhibitor, an immunosuppressant, a macrolide, cyclosporin A, an antiinflammatory, a slow-acting antirheumatic drug, a local anesthetic, an antipyretic, an analgesic, a nonacidic analgesic/antiinflammatory, an antiarrhythmic, a $Ca^{++}$ antagonist, an antihistaminic, a sympathomimetic, a human urokinase inhibitor, or a compound that alters the pleiotropic resistance to cytostatics; or a salt of any of the foregoing.

2. The compound according to claim 1, wherein glycosyl is a glucuronic acid,

W is phenyl,

R is a hydrogen atom, CN, nitro, fluorine, chlorine, bromine, p is zero, n is an integer zero, 1 or 2, Y is an oxygen atom, Z is —$N(CH_3)$—, —$C(CH_3)_2$—NH—, —$CH(CH_3)$—NH—, —$C(CH_3)_2$—$N(C_1-C_4)alkyl)$—, —$CH(CH_3)$—$N(C_1-C_4)alkyl)$—.

3. The compound according to claim 1, wherein the glycosyl is a monosaccharide.

4. The compound according to claim 3, wherein the glycosyl is D-glucuronyl, L-iduronyl, D-glucopyranosyl-, D-galactopyranosyl, N-acetyl-D-glucosaminyl-, N-acetyl-D-galactosaminyl-, D-mannopyranosyl- or L-fucopyranosyl.

5. The compound according to claim 1, wherein the glycosyl is cleavable by induronidase, glucosidase, galactosidase, N-acetyl-D-glucosaminidase, N-acetyl-D-galactosaminidase, mannosidase, fucosidase or glucuronidase.

6. The compound according to claim 5, wherein the glycosyl is cleavable by β-glucuronidase.

7. The compound according to claim 1, wherein the compound is

2-[N-methyl-N-[(4-(N,N'-bis(2-chloroethyl)amino)phenyloxy-carbonyl]amino]-4-nitrophenyl-β-D-glucuronic acid, 2-[N-methyl-N-[(4-(N,N'-bis(2-iodoethyl)amino)phenyloxy-carbonyl]amino]-4-nitrophenyl-β-D-glucuronic acid,

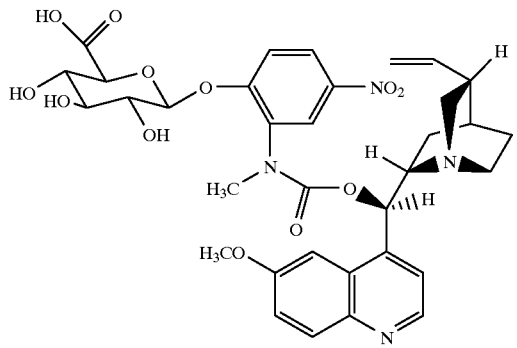

or

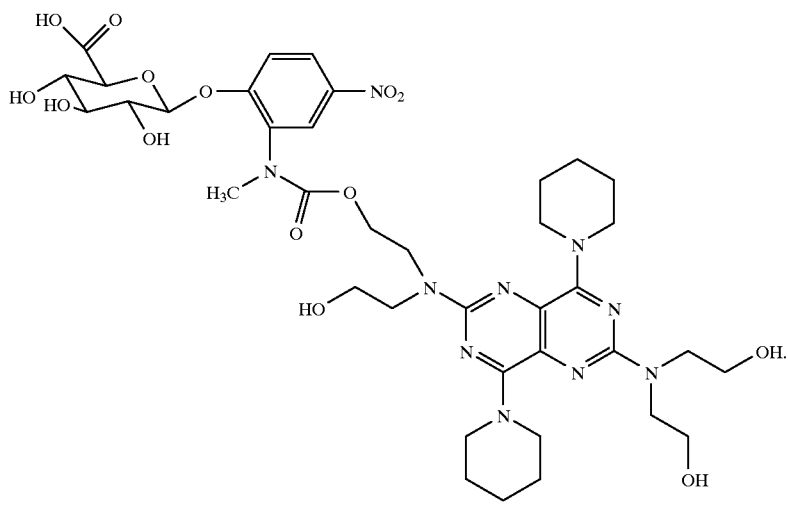

8. A process of preparing a compound according to claim 1, comprising reacting a compound of the formula II $$\text{glycosyl-Y}[-C(=Y)-X-]_p-W(R)_n-Z \qquad (II)$$

in which the radicals glycosyl, Y, X, p, W, R, n and Z are defined as for formula I in claim 1, with an active compound which has an activated carboxyl, amino or imino radical, in the presence of a solvent selected from the group consisting of acetonitrile, dioxane, tetrahydrofuran, dichloromethane, dimethylformamide and acetone.

9. The process according to claim 8, wherein the glycosyl is a glucuronic acid,

W is phenyl,

R is a hydrogen atom, CN, nitro, fluorine, chlorine, bromine, p is zero, n is an integer zero, 1 or 2, Y is an oxygen atom, z is —N(CH$_3$)—, —C(CH$_3$)$_2$—NH—, —CH(CH$_3$)—NH—, —C(CH$_3$)$_2$—N(C$_1$-C$_4$)alkyl)—, —CH(CH$_3$)—N(C$_1$-C$_4$)alkyl)—.

10. A pharmaceutical composition, comprising a compound according to claim 1.

11. The pharmaceutical composition according to claim 10, wherein the glycosyl is a glucuronic acid, W is phenyl, R is a hydrogen atom, CN, nitro, fluorine, chlorine, bromine, p is zero, n is an integer zero, 1 or 2, Y is an oxygen atom, Z is —N(CH$_3$)—, —C(CH$_3$)$_2$—NH—, —CH(CH$_3$)—NH—, —C(CH$_3$)$_2$—N(C$_1$-C$_4$)alkyl)—, —CH(CH$_3$)—N(C$_1$-C$_4$)alkyl)—.

12. The pharmaceutical composition according to claim 10, comprising a pharmaceutically suitable and physiologically tolerable excipient.

13. A method for treating a carcinomatous disease or inflammatory disease with a compound according to claim 1.

14. The method according to claim 13, wherein the disease is an autoimmune disease or a chronic inflammatory disease.

15. The method according to claim 14, wherein the disease is rheumatoid arthritis.

16. The method according to claim 13, wherein the glycosyl is a glucuronic acid, W is phenyl, R is a hydrogen atom, CN, nitro, fluorine, chlorine, bromine, p is zero, n is an integer zero, 1 or 2, Y is an oxygen atom, Z is —N(CH$_3$)—, —C(CH$_3$)$_2$—NH—, —CH(CH$_3$)—NH—, —C(CH$_3$)$_2$—N(C$_1$-C$_4$)alkyl)—, —CH(CH$_3$)—N(C$_1$-C$_4$)alkyl)—.

* * * * *